US009448193B2

(12) United States Patent
Mangematin et al.

(10) Patent No.: US 9,448,193 B2
(45) Date of Patent: Sep. 20, 2016

(54) METHOD AND DEVICE FOR DETERMINING THE HEAT LOSS COEFFICIENT OF A PREMISES

(75) Inventors: Eric Mangematin, Cires les Mello (FR); Guillaume Pandraud, Paris (FR); Jerome Gilles, Cambridge, MA (US); Didier Roux, Courbevoie (FR)

(73) Assignee: SAINT-GOBAIN ISOVER, Courbevoie (FR)

( * ) Notice: Subject to any disclaimer, the term of this patent is extended or adjusted under 35 U.S.C. 154(b) by 794 days.

(21) Appl. No.: 13/820,364

(22) PCT Filed: Sep. 2, 2011

(86) PCT No.: PCT/FR2011/052016
§ 371 (c)(1),
(2), (4) Date: May 8, 2013

(87) PCT Pub. No.: WO2012/028829
PCT Pub. Date: Mar. 8, 2012

(65) Prior Publication Data
US 2013/0226503 A1 Aug. 29, 2013

(30) Foreign Application Priority Data

Sep. 3, 2010 (FR) .................................. 10 57033

(51) Int. Cl.
*G06F 11/00* (2006.01)
*G01N 25/00* (2006.01)
*G01K 17/20* (2006.01)
(52) U.S. Cl.
CPC ............... *G01N 25/00* (2013.01); *G01K 17/20* (2013.01)

(58) Field of Classification Search
CPC ..................... E21B 43/2401; A61B 17/00577
USPC .................................. 702/136, 130, 182–185
See application file for complete search history.

(56) References Cited

U.S. PATENT DOCUMENTS 5,833,365 A * 11/1998 Stals et al. ........................ 374/5

FOREIGN PATENT DOCUMENTS

FR 2 907 215 4/2008
NL 1035399 6/2008

OTHER PUBLICATIONS

International Search Report Issued Jan. 17, 2012 in PCT/FR11/052016 Filed Sep. 2, 2011.

*Primary Examiner* — Edward Raymond
(74) *Attorney, Agent, or Firm* — Oblon, McClelland, Maier & Neustadt, L.L.P

(57) ABSTRACT

A method determining heat loss coefficient K of a premises, includes: in unoccupied premises, performing a campaign of measurements of at least one temperature inside the premises $T_{ik}$ at closely-spaced time intervals over at least two successive time periods $D_k$ corresponding to distinct heating powers $P_{totk}$ of the premises; determining temperature of outside air $T_{ek}$ at the same closely-spaced times; for each time period $D_k$, on the basis of evolution $T_{ik}(t)$ of a quantity $T_{ik}$ as a function of time, selecting a time interval $\Delta t_k$ for which the evolution $T_{ik}(t)$ is substantially linear, then determining the slope $\alpha_k$ of the tangent to the evolution $T_{ik}(t)$ over this time interval $\Delta t_k$, and deducing the value of the heat loss coefficient K of the premises on the basis of the slopes $\alpha_k$.

15 Claims, 5 Drawing Sheets

METHOD AND DEVICE FOR DETERMINING THE HEAT LOSS COEFFICIENT OF A PREMISES

BACKGROUND

The present invention relates to a method and a device for determining the heat loss coefficient of a premises. Within the meaning of the invention, a premises is an individual house or a building, in particular for residential or tertiary use, or else a part of such a building, for example an apartment in a building with multiple floors.

The heat loss coefficient of a premises, denoted K, is equal to the heat loss power of the premises (in Watts) per degree (Kelvin or Celsius) of difference between the temperature of the air inside the premises and the temperature of the outside air. This coefficient K is representative of the energy performance of the envelope of the premises.

The heat loss coefficient K of a premises is influenced, on the one hand, by the heat losses by transmission through the walls of the premises and, on the other hand, by infiltrations of air. The heat losses by transmission are represented by a factor $H_T=UA_T$, where U is the heat transfer coefficient of the envelope of the premises, also called the specific heat transfer coefficient of the premises, and $A_T$ is the total area of the walls of the premises. The infiltrations of air into the premises are represented by a factor m'.Cp, where m' is the air renewal flow rate and Cp is the heat capacity of the air. Consequently, the heat loss coefficient K is given by the relation:

$$K=H_T+m'.Cp=UA_T+m'.Cp.$$

The coefficient U is used, within the framework of thermal regulations such as RT 2005 in France or the regulation EnEV in Germany, to estimate the overall energy consumption of the premises. Its determination is useful in order to perform a diagnosis of the thermal insulation of a premises, in particular after its construction, to verify that the constructor has adhered to the standards in force in terms of thermal insulation both in terms of choice of materials and their implementation, or when a refurbishment of the premises is considered, with a view to evaluating the measures that should be taken to improve the thermal performance.

It is known to determine the heat loss coefficient of a premises by means of computational softwares which involve modeling the envelope of the premises. Such softwares are relatively tricky to implement and have the drawback of providing only a theoretical result, which does not assess such real parameters as the effective implementation of the insulation materials, the construction technology, etc.

Moreover, it is known to determine the heat loss coefficient of a premises by carrying out in situ measurements in the premises over long periods, which generally extend over several weeks or months, and then by undertaking a statistical analysis of these measurements. The statistical analysis is made necessary by the multiplicity of parameters which influence the thermal behavior of the premises over the measurement period, in particular the meteorological conditions and the occupancy conditions of the premises. These known in situ measurement methods have the drawback of being lengthy and of involving significant and expensive equipment.

BRIEF SUMMARY

It is these drawbacks that the invention is intended more particularly to remedy by proposing a method and a device making it possible to determine in a fast manner the heat loss coefficient of a premises, with moderate cost and reasonable accuracy.

For this purpose, one subject of the invention is a method for determining the heat loss coefficient K of a premises, characterized in that it comprises steps in which:
  in the unoccupied premises, a campaign of measurements of at least one temperature inside the premises $T_{ik}$ at closely-spaced time intervals is performed over at least two successive time periods $D_k$ corresponding to distinct heating powers $P_{totk}$ of the premises;
  the temperature of the outside air $T_{ek}$ at said same closely-spaced times is determined;
  for each time period $D_k$, on the basis of the evolution $T_{ik}(t)$ of the quantity $T_{ik}$ as a function of time, this evolution is quantitatively analyzed through a simple mathematical model:
    either, if there exists a time interval $\Delta t_k$ for which the evolution $T_{ik}(t)$ is substantially linear, the slope $\alpha_k$ of the tangent to the curve $T_{ik}(t)$ is determined over this time interval $\Delta t_k$ and the value of the heat loss coefficient K of the premises is deduced on the basis of the slopes $\alpha_k$;
    or, if there does not exist any time interval for which the evolution $T_{ik}(t)$ is substantially linear, a time interval $\Delta t_k'$ is selected over which the evolution $T_{ik}(t)$ is substantially exponential of type $\exp(-t/\tau)$, with $\tau$ the thermal time constant of the premises, and the value of the heat loss coefficient K of the premises is deduced, which is the value such that the curve $$\mathrm{Ln}\left[\left(\theta_k(t)-\frac{P_{totk}}{K}\right)\bigg/\left(\theta_k(0)-\frac{P_{totk}}{K}\right)\right]$$

is a straight line, where $\theta_k(t)=T_{ik}(t)-T_{ekm}'$ with $T_{ekm}'$ the average of the temperature measurements of the outside air $T_{ek}$ over the time interval $\Delta t_k'$.

The principle underlying the invention is to use the transient variations of the inside temperature of the premises subjected to controlled internal impulses and in a measured external environment. Quantitative analysis of the variation of the inside temperature of the premises makes it possible to quantitatively determine the energy efficiency of the premises over a short period, extending over a few hours, while limiting the number of parameters liable to influence the thermal behavior of the premises. In particular, the brevity of the measurements makes it possible to circumvent the influence of the conditions of use of the premises and of the variations of the outside climatic conditions.

Of course, the method according to the invention does not necessarily require the setting up of a graphical representation of the evolution $T_{ik}(t)$.

In particular, in the case where there exists a time interval $\Delta t_k$ for which the evolution $T_{ik}(t)$ is substantially linear, the slope $\alpha_k$ of the tangent to the curve $T_{ik}(t)$ over the time interval $\Delta t_k$ is equal to the derivative of the evolution $T_{ik}(t)$ over this interval $\Delta t_k$. Hence, the step of determining the slope $\alpha_k$ of the tangent to the curve $T_{ik}(t)$ over the time interval $\Delta t_k$ may be carried out, within the framework of the invention, by computing the derivative of the evolution $T_{ik}(t)$ over the time interval $\Delta t_k$, without resorting to a graphical representation of the evolution $T_{ik}(t)$.

In the same manner, in the case where there does not exist any time interval for which the evolution $T_{ik}(t)$ is substantially linear, the determination of the value of the heat loss coefficient K of the premises such that the curve $$Ln\left[\left(\theta_k(t) - \frac{P_{totk}}{K}\right) \Big/ \left(\theta_k(0) - \frac{P_{totk}}{K}\right)\right]$$

is a straight line does not necessarily involve a graphical representation of this curve, and can be done via a mathematical linearization of the evolution $$Ln\left[\left(\theta_k(t) - \frac{P_{totk}}{K}\right) \Big/ \left(\theta_k(0) - \frac{P_{totk}}{K}\right)\right].$$

The computation steps of the method, in particular for the determination of the slopes $\alpha_k$ or for the linearization of the evolution $$Ln\left[\left(\theta_k(t) - \frac{P_{totk}}{K}\right) \Big/ \left(\theta_k(0) - \frac{P_{totk}}{K}\right)\right],$$

may be implemented with the aid of any appropriate computation means. This may entail in particular an electronic computation unit comprising at the same time means for acquiring the measurements of temperature inside the premises $T_{ik}$ and means for computing the heat loss coefficient K of the premises on the basis of these measurements.

According to the invention, the expression "heating power of the premises" is intended to mean any operative condition generating a variation of the inside temperature of the premises for given conditions of outside temperature. It is understood that the heating power $P_{totk}$ may be positive, zero or negative. A positive heating power corresponds to a supply of heat into the premises, whilst a negative heating power corresponds to a supply of cold into the premises. In the case of a zero heating power, the variation of the inside temperature of the premises may result from a difference between the inside temperature of the premises and the outside temperature, or else from a variation of the outside temperature. According to the invention, provision is made for at least one of the heating powers $P_{totk}$ to be non-zero.

In an advantageous manner, for each time period $D_k$, the heating power $P_{totk}$ of the premises comprises an imposed heating power $P_{impk}$ imposed by means of a controlled power source. If no power source other than that used to apply the imposed heating power $P_{impk}$ is active in the premises in the course of the time period $D_k$, the total heating power $P_{totk}$ of the premises is equal to the imposed heating power $P_{impk}$. If on the other hand there exists, in the course of the period $D_k$, an additional power $P_{supk}$ in the premises supplementing the power $P_{impk}$, the total heating power of the premises is equal to $P_{impk}+P_{supk}$. In particular, in the case where the solar radiation over the time period $D_k$ is significant, the contribution of the solar radiation to the heating of the premises forms part of the additional power $P_{supk}$.

In practice, the conditions of implementation of the method are adapted so as to limit the supplies of additional power $P_{supk}$ other than the imposed heating power $P_{impk}$, in particular by taking care that the premises is unoccupied.

In an advantageous manner, the method is implemented over time periods $D_k$ for which the solar radiation is weak, preferably zero. In a preferred manner, the method is implemented over time periods $D_k$ chosen during the night, or optionally in the daytime in the morning or the evening. It is thus possible to reduce the contribution of the solar radiation and to limit the fluctuations of the temperature of the outside air.

The time periods $D_k$ may be either disjoint, or follow one another in immediate succession. In the latter case, it may be considered that the method is carried out in its entirety over a continuous time period, formed by the succession of time periods $D_k$. Preferably, with a view to limiting the implementation time of the method while reducing the contribution of the solar radiation, the method is carried out in its entirety continuously over a single nocturnal period.

Preferably, over each time period $D_k$, any fixed ventilation system fitted to the premises is deactivated and all the ventilation inlets are closed or plugged, so as to limit the exchanges of air with the outside.

As a variant, the fixed ventilation systems of the premises can operate in the course of the method over each time period $D_k$. However, this introduces an additional term relating to air renewal into the expression for the heat loss coefficient K:

$$K = H_T + m'_1 . Cp + m'_2 . Cp,$$

where $m'_1$ the renewal flow rate of air by infiltration and $m'_2$ the renewal flow rate of air due to the fixed ventilation systems are correlated, the value of one depending on the value of the other.

The method according to the invention rests upon a modeling of the premises in the form of an isothermal box characterized, on the one hand, by its heat loss coefficient K, and, on the other hand, by its inertia or its effective heat capacity C. The effective heat capacity C of a premises, which corresponds to the heat capacity of the materials situated in the insulating envelope of the premises, is defined as the energy necessary to increase the ambient temperature of the premises by 1 K at constant outside temperature.

In a general manner, for each time period $D_k$, the energy balance of the premises may be written:

$$K(T_{ik} - T_{ek}) + C\frac{d(T_{ik} - T_{ek})}{dt} = P_{totk} \qquad (1)$$

with
K the heat loss coefficient of the premises,
$T_{ik}(t)$ the inside temperature of the premises,
$T_{ek}(t)$ the temperature of the outside air,
C the effective heat capacity of the premises,
$P_{totk}$ the total heating power of the premises.
Equation (1) admits as solution:

$$T_{ik}(t) - T_{ek}(t) = \frac{P_{totk}}{K} + \left[(T_{ik}(0) - T_{ek}(0)) - \frac{P_{totk}}{K}\right]e^{\frac{-K \cdot t}{C}}.$$

This solution may be linearized to short times:

$$T_{ik}(t) - T_{ek}(t) = \frac{P_{totk}}{K} + \left[(T_{ik}(0) - T_{ek}(0)) - \frac{P_{totk}}{K}\right]\left[\frac{-K \cdot t}{C}\right].$$

The slope $\alpha_k$ of the tangent to the curve representative of the evolution of the quantity $T_{ik}-T_{ek}$ as a function of time is then:

$$\alpha_k = \frac{P_{totk}}{C} - (T_{ik}(0) - T_{ek}(0))\frac{K}{C}.$$

In practice, within the framework of the method of the invention, within the time period $D_k$, a time interval $\Delta t_k$ is sought for which the evolution $T_{ik}(t)$ is substantially linear. Over this time interval $\Delta t_k$, it may be considered that the temperature of the outside air $T_{ek}$ is substantially constant and equal to the mean temperature over the time interval $\Delta t_k$, denoted $T_{ekm}$. Furthermore, as a time interval $\Delta t_k$ is selected in the heating period $D_k$, the exact positioning of the time t=0 with respect to the heating period is arbitrary and it is preferable to consider a mean value $T_{ikm}$ of $T_{ik}(t)$ over the time interval $\Delta t_k$ in the expression for the slope $\alpha_k$. Hence, the slope $\alpha_k$ of the curve $\theta_k(t)=T_{ik}(t)-T_{ekm}$ over the time interval $\Delta t_k$, which is equal to the slope of the curve $T_{ik}(t)$ over the time interval $\Delta t_k$, is, in this linear approximation:

$$\alpha_k = \frac{P_{totk}}{C} - \theta_{km}\frac{K}{C}, \text{ with } \theta_{km} = T_{ikm} - T_{ekm}.$$

If the value of the effective heat capacity of the premises C is known, the value of the heat loss coefficient K of the premises is thus derived directly.

If the value of the effective heat capacity of the premises C is not known, the value of the heat loss coefficient K of the premises can be derived by applying over two successive time periods, two heating powers $P_{imp1}$ and $P_{imp2}$ of different values, and by measuring the evolution of at least one temperature inside the premises $T_{i1}(t)$ or $T_{i2}(t)$ over each of these two time periods. The value of the coefficient K can then be obtained by selecting a time interval $\Delta t_1$ or $\Delta t_2$ for which the evolution $T_{i1}(t)$ or $T_{i2}(t)$ is substantially linear, and by determining, over this time interval $\Delta t_1$ or $\Delta t_2$, the slope $\alpha_1$ or $\alpha_2$ of the tangent to the curve $(T_{ik}(t))_{k=1 \text{ or } 2}$. The ratio of the slopes $$\frac{\alpha_1}{\alpha_2}$$

leads to the value of the heat loss coefficient K of the premises by removing the dependency with regard to the effective heat capacity of the premises C:

$$\frac{\alpha_1}{\alpha_2} = \frac{P_{tot1} - \theta_{1m} \cdot K}{P_{tot2} - \theta_{2m} \cdot K}. \quad (2)$$

More precisely, the method for determining the heat loss coefficient K of the premises then comprises steps in which:
in the unoccupied premises and over two successive time periods $D_1$ and $D_2$ are performed:
i. over the first time period $D_1$, the application of a first imposed heating power $P_{imp1}$ of the premises by means of a controlled power source, and a campaign of measurements of at least one temperature inside the premises $T_{i1}$ at closely-spaced time intervals, as well as the determination of the temperature of the outside air $T_{e1}$ at said same closely-spaced times, and then
ii. over the second time period $D_2$, the application of a second imposed heating power $P_{imp2}$ of the premises by means of a controlled power source, where the second imposed heating power $P_{imp2}$ is different from the first power $P_{imp1}$, and a campaign of measurements of at least one temperature inside the premises $T_{i2}$ at closely-spaced time intervals, as well as the determination of the temperature of the outside air $T_{e2}$ at said same closely-spaced times;
for each of the first and second time periods $D_1$ and $D_2$, a time interval $\Delta t_1$ or $\Delta t_2$ is selected for which the evolution $T_{i1}(t)$ or $T_{i2}(t)$ is substantially linear and the slope $\alpha_1$ or $\alpha_2$ of the tangent to the curve $(T_{ik}(t))_{k=1 \text{ or } 2}$ over this time interval $\Delta t_1$ or $\Delta t_2$ is determined;
the value of the heat loss coefficient K of the premises is deduced on the basis of the ratio of the slopes $$\frac{\alpha_1}{\alpha_2}.$$

According to a feature of the invention, the difference between the imposed heating powers $P_{imp1}$ and $P_{imp2}$ is maximized. In an advantageous manner, one from among the powers $P_{imp1}$ and $P_{imp2}$ is a zero power, whilst the other power is a strictly positive power making it possible to obtain a variation of the inside temperature $T_{ik}$ of at least 1° C. over a time interval $\Delta t_k$ for which the evolution $T_{ik}(t)$ is substantially linear. Over the time period corresponding to the application of the non-zero imposed heating power, the rise in temperature of the premises as a function of time is measured. Over the time period corresponding to the application of the zero imposed heating power, this corresponding to an absence of heating in the premises, the fall in temperature of the premises as a function of time is measured. The heat loss coefficient K of the premises is then determined on the basis of the ratio of the slopes of the temperature rise and fall curves of the premises.

Preferably, for each time period $D_k$, the campaign of measurements of the inside temperature of the premises $T_{ik}$ is carried out over a time period sufficient to obtain a variation of the inside temperature $T_{ik}$ of at least 1° C., preferably of between 1° C. and 10° C.

By way of example, it is possible to perform successively the application of the zero first imposed heating power $P_{imp1}$, corresponding to an absence of heating in the premises, and then the application of the non-zero second imposed heating power $P_{imp2}$.

As a variant, the non-zero imposed heating power, which generates a temperature rise, may be applied prior to the zero imposed heating power, that is to say the stopping of the heating in the premises, which generates a temperature fall.

According to an advantageous feature, the controlled power source for the heating of the premises may be a fixed item of equipment of the premises, that is to say a heating means installed in the premises independently of the implementation of the method, provided that this heating means is sufficiently powerful to ensure fast heating of the premises and that the power delivered can be measured accurately.

This may in particular entail a heat pump whose coefficient of performance (COP) is known. The COP, which is the ratio of the thermal power produced to the electrical power consumed, is customarily of the order of 3 to 5. The COP varies with the temperatures of the cold and hot sources. Now, whereas the hot source is regulated and exhibits a substantially constant temperature, the cold source is for its part generally taken outside and is therefore not controllable. The determination of the temperature of the outside cold source over a time period encompassing the period of implementation of the method of the invention makes it possible to adjust the value of the COP more accurately.

As a variant, the controlled power source for the heating of the premises may be a source brought into the premises specifically for the implementation of the method.

The heating elements for the premises may be of convective, conductive or radiative type, or may combine several of these technologies. Preferably, the heating elements are electrical appliances, thereby making it possible to determine the heating power directly and accurately. Examples of electrical heating appliances comprise in particular appliances of convective type involving the blowing of air heated by means of electrical resistances; heating blankets or heating films, in particular deposited against the walls of the premises; parasol radiant heaters. As a variant, the heating elements may be appliances that operate using gas or fuel oil, provided that the efficiencies of the burners and the fuel flow rates can be estimated sufficiently accurately to derive the heating power.

In an advantageous manner, when the heating elements for the premises are of convective type, it is possible to combine these heating elements, which ensure heat dissipation, with at least one fan, which ensures good spatial distribution of the heat. Such a heating assembly combining heating elements of convective type and fans makes it possible to guarantee homogeneous heating of the premises.

Preferably, the source for the heating of the premises is chosen to allow heating which ensures that the mean temperature of the walls inside the premises is substantially equal to the temperature of the ambient air inside the premises. In practice, this condition is fulfilled when the heating elements, fixed or brought into the premises specifically for the method, heat the mass of the premises directly, that is to say the heat capacity of the premises, and not only the air inside the premises. Direct heating of the mass of the premises, which may be obtained for example by means of a fixed floor-based heating system of the premises, or else by means of heating films added onto the floor of the premises, is therefore generally preferable to heating of convective type which heats the air inside the premises by priority.

FIGS. 1 and 2 annexed illustrate the advantages, for obtaining homogeneous heating of a premises, of the use of a heating system which heats the mass of the premises directly, rather than a heating system of convective type. These figures show the curves of air temperature rise in various rooms of a 5-room two-storey house, respectively in the case of heating by means of electric convectors for FIG. 1 and in the case of heating by means of electrical heating films for FIG. 2.

In the case of FIG. 1, an electric convector is placed at the center of each measured room of the house, with a temperature setting of 31° C. In the case of FIG. 2, the floor of each measured room of the house is covered with heating films of 150 W/m² power, marketed by the company DOMOTECK in the "Aluminium Mat" range, with a temperature setting of 31° C. The results of FIGS. 1 and 2 correspond to one and the same total heating power dissipated in the house, respectively by the electric convectors for FIG. 1 and by the heating films for FIG. 2. For FIGS. 1 and 2, the temperature measurements are carried out, in each measured room of the house, with the aid of a thermocouple positioned in the ambient air at the center of the room at a height of 160 cm.

As emerges from a comparison of FIGS. 1 and 2, heating using heating films makes it possible to achieve better temperature homogeneity in all the rooms of the house than convective heating. In particular, with heating using heating films, fewer disparities are observed between the temperatures of the first-floor rooms, on the one hand, and the temperatures of the second-floor rooms, on the other hand. It is also noted that the slopes of the temperature rise curves are more homogeneous from one room to another with the heating using heating films, this being particularly sought-after within the framework of the method according to the invention. These two advantages, namely better temperature homogeneity and better homogeneity in the temperature rise slopes, originate from the fact that the mass of the house is heated directly in the case of heating using heating films.

According to an advantageous feature, each campaign of measurements of the temperature inside the premises comprises measurements of the ambient temperature inside the premises, measurements of the temperature of walls of the premises and/or measurements of the radiant mean temperature inside the premises. In practice, any known measurement method may be used to derive these temperatures, in particular the measurement methods described in the standard NF EN ISO 7726. By way of example, the measurements of the ambient temperature inside the premises and of the temperature of the walls of the premises may be carried out with the aid of thermocouples or, preferably, Pt100 probes. For the measurements of the radiant mean temperature inside the premises, a black globe thermometer may advantageously be used.

Preferably, at least the temperature of a wall inside the premises is measured. When the heating of the premises ensures that the ambient temperature is sufficiently close to the temperature of the walls inside the premises, which may be obtained in particular with a heating which heats the mass of the premises by priority, a measurement of the ambient temperature inside the premises may be substituted for the measurement of the wall temperature inside the premises.

If the heating of the premises is very homogeneous, so that the inside temperature is the same throughout the premises, or in all the rooms of the premises if the latter comprises internal partitions, then the measurements of the temperature inside the premises may be limited to measurements inside a single room of the premises.

If the method of the invention is implemented in a premises for which the heating is less homogeneous, it may be envisaged to measure the temperature in several rooms of the premises and to consider that the temperature inside the premises at each time t is the average of the temperature measurements obtained at the time t in the various rooms of the premises, on condition that they are not too different, which would indicate a lack of ventilation of the premises. Provision may also be made for several different temperature measurements in each room of the premises. Thus, provision may be made to carry out in each room at the same time a measurement of the ambient temperature and/or a measurement of the temperature of a wall of the envelope of the premises and/or a measurement of the radiant mean temperature.

According to an advantageous feature, the determination of the temperature of the outside air $T_{ek}$ takes place, within the framework of the method of the invention, by way of a campaign of measurements which are simultaneous with the measurements of the inside temperature of the premises $T_{ik}$, that is to say at the same closely-spaced times.

As a variant, the determination of the temperature of the outside air $T_{ek}$ at these closely-spaced times may be obtained by interpolation of meteorological data local to the premises.

Preferably, the method according to the invention is implemented over a time period for which the temperature of the outside air $T_{ek}$ is stable.

When the variation of the temperature of the outside air $T_{ek}(t)$ is significant during the implementation of the method, this variation can be taken into account by regarding it as a linear evolution, thus resulting in a non-linearity of the evolution of the inside temperature of the premises $T_{ik}(t)$. The curve $\theta_k(t)=T_{ik}(t)-T_{ek}(t)$ can then be modeled as a second-degree polynomial whose coefficients involve the characteristics K and C of the premises. In this case, it is possible to determine K and C by applying a single imposed heating power $P_{impk}$ of the premises, with a single campaign of measurements of the temperature inside the premises $T_{ik}$, since, by expanding the solution of equation (1) to second order, equality is obtained between two second-degree polynomials, with equality for the term in t and equality for the term in $t^2$. Such an expedient is however less preferred, because of its greater complexity.

As explained previously, the heat loss coefficient K determined in accordance with the invention integrates the contributions of the heat losses by transmission and infiltrations of air, that is to say:

$$K = H_T + m'.Cp = UA_T + m'.Cp.$$

If it is desired to derive the heat transfer coefficient U of the premises, it is possible to decouple the contribution of the heat losses by transmission, on the one hand, and that of the air infiltrations, on the other hand, by evaluating the renewal flow rate of the air m' in the premises.

When no fixed ventilation system of the premises is active in the course of the method for determining the coefficient K, the flow rate m' is equal to the renewal flow rate of the air by infiltration. This flow rate m' may be determined by any appropriate scheme, in particular by a detection scheme based on tracer gases or by a blower door infiltrometry test.

In an advantageous manner, the detection scheme based on tracer gases provides an instantaneous value of the flow rate m'. This scheme based on tracer gases also makes it possible to take accurate account of the contribution of the ventilation in the energy balance of the premises, this being advantageous in cases where the method is implemented whilst a ventilation system fitted to the premises is active, in particular in cases where it is not possible to deactivate, prior to the implementation of the method, the fixed ventilation systems fitted to the premises.

If one opts for a blower door test, it is possible to compute a mean value of the flow rate m' on the basis of the measured value of the leakage flow rate.

By way of example, if a blower door test is carried out in which the indicator n50 is measured such as defined in the standard NF EN 13829, that is to say the leakage flow rate under 50 Pa divided by the heated volume of the premises, it is known to deduce the value of the air renewal flow rate m' on the basis of the measured value of the n50, by using the rule established by Drubul:

$$m' = \frac{n50 \cdot V}{20}, \quad (3)$$

where V is the heated volume of the premises.

As a variant, the mean value of the air renewal flow rate m' may be obtained on the basis of the measurement of indicators other than the indicator n50, or else with the aid of regulatory computation schemes other than that involving relation (3) hereinabove. In particular, an alternative approach to Drubul's rule for determining the value of the air renewal flow rate m' on the basis of the measured value of the n50 consists in estimating the air infiltration rate based on the empirical model proposed in the standard NF EN ISO 13790, annex G.

When a fixed ventilation system of the premises is active in the course of the method for determining the coefficient K, the flow rate m' incorporates the contribution of air renewal due to this ventilation system, that ought to be taken into account in addition to the air renewal by infiltration. The air renewal flow rate due to the fixed ventilation system may be determined by measuring the air flow rate at each ventilation vent.

When the trials are carried out by preferentially heating the mass rather than the interior air of the premises, or when the heat loss coefficient is computed with the aid of wall temperatures rather than temperatures of the ambient air, the computed loss coefficient $K_{calc}$ is not perfectly representative of the actual losses, since it takes no account of the heat exchange between the wall and the ambient air. This may be partially corrected by determining the convecto-radiative exchange coefficient $h_i$. The coefficient $h_i$ may be estimated through the knowledge of the ambient and black globe inside temperatures of the premises, as well as of the air speed, on the basis of the following relation, defined in RT 2005: $h_i = 2.5 + 4.\sigma.\epsilon_i.T_{mi}^3$, where $T_{mi}$ is the radiant mean temperature which, in accordance with the standard NF EN ISO 7726, is related, for a standard globe 85 mm in diameter and with emissivity 0.95, to the globe temperature $T_g$, the ambient temperature $T_\alpha$ and the speed of the air $v_\alpha$:

$$T_{mi} = [(T_g+273)^4 + 2.5 \times 10^8 \times v_\alpha^{0.6}(T_g-T_\alpha)]^{1/4} - 273.$$

As a variant, if the radiant mean temperature $T_{mi}$ is not available, the convective exchange coefficient $h_i$ may be assumed known. In particular, the convective exchange coefficient $h_i$ may be estimated as being of the order of 8 $W/m^2.K$, which is the order of magnitude given by RT 2005 in the Th-U rules.

The corrected loss coefficient $K_{corr}$ then equals:

$$\frac{1}{K_{corr}} = \frac{1}{K_{calc}} + \frac{1}{h_i A_T}. \quad (4)$$

One subject of the invention is also a device for the implementation of a method such as described hereinabove, comprising at least one temperature sensor which measures a temperature inside the premises $T_{ik}$ and a heating device for homogeneous heating of the premises comprising a controlled power source.

According to an advantageous feature of such a device, the heating device heats the mass of the premises directly, that is to say the heat capacity of the premises and not only the air inside the premises, and the temperature sensor measures the temperature in the air inside the premises. As mentioned previously, examples of heating devices which heat the mass of the premises directly comprise heating films added on the floor of the premises or else fixed floor-based heating systems of the premises.

The selection of a device which combines direct heating of the mass of the premises and measurement of the temperature in the air inside the premises is particularly advantageous for the implementation of the method according to the invention. Indeed, if it is chosen to carry out measurements of wall temperature, it is necessary, in order to obtain a good estimation of the mean temperature in a room, to carry out measurements of temperatures on several walls of the room, and then to determine an average of these temperatures of walls, and to do so whatever the homogeneity of the heating. Conversely, if it is chosen to carry out measurements of air temperature, a single measurement in the air volume substantially at the center of the room suffices to obtain a value representative of the mean temperature in the room, on condition that the heating is sufficiently homogeneous. Measurement of temperature in the air therefore makes it possible to reduce the number of measurements to be performed within the framework of the method according to the invention, provided that it is carried out in a room heated in a globally homogeneous manner. Now, as explained previously, homogeneous heating is obtained more easily and more rapidly with a heating device which heats the mass of the premises directly, rather than with a convective heating device which heats the air inside the premises by priority. Hence, by combining direct heating of the mass of the premises and measurement of the temperature in the air inside the premises, the implementation of the method according to the invention is simplified and its duration is limited.

According to another advantageous feature, the device furthermore comprises an electronic central unit comprising means for acquiring the temperature measurements inside the premises, means for computing the heat loss coefficient K of the premises on the basis of the acquired temperature measurements and means of automatic control of the power source as a function of the acquired temperature measurements.

An automatic control device such as this uses the temperature signals acquired, not only to compute the heat loss coefficient K of the premises, but also to automatically drive the power source ensuring the heating of the premises. In an advantageous manner, the processing of the temperature information is ensured by the electronic central unit, which is associated with control software internal to the device which is parametrized in such a way that any temperature evolution corresponding to predefined criteria of the method according to the invention, in particular criteria describing the linearity of the evolution $T_{ik}(t)$ over a time interval, the stability of the temperature of the outside air $T_{ek}$, etc., makes it possible to control the intensity of the heating power in the premises.

By way of example, a test that might be run in an autonomous manner by an automatic control device such as this comprises the following sequence of steps:
  running of the procedure;
  turning on of the heating device;
  when the evolution $T_{i1}(t)$ of the temperature measured inside the premises in the course of the heating of the premises is substantially linear and the temperature of the outside air $T_{e1}$ is stable with regard to the predefined criteria, computation and storage of the value of the slope $\alpha_1$ of the tangent to the heating curve $T_{i1}(t)$ and turning off of the heating device;
  when the evolution $T_{i2}(t)$ of the temperature measured inside the premises in the course of the cooling of the premises is substantially linear and the temperature of the outside air $T_{e2}$ is stable with regard to the predefined criteria, computation and storage of the value of the slope $\alpha_2$ of the tangent to the cooling curve $T_{i2}(t)$;
  on the basis of the stored values of the slopes $\alpha_1$ and $\alpha_2$, computation of the heat loss coefficient K of the premises.

The heating device of the automatic control device may be a heating device tied to the premises tested or a heating device added specifically for carrying out the trials. Likewise, the temperature measurement sensors of the automatic control device may be tied to the premises or add-ons. As explained previously, the temperature measurement sensors are preferably sensors for measuring the temperature in the air inside the premises, rather than sensors for measuring the temperature of walls inside the premises.

According to an advantageous feature, the control software internal to the device is designed in such a way that each test run in an autonomous manner by the automatic control device is run preferably at night, and, if previous measurements have already been carried out, the automatic control device optimizes the cycle of each test so as to minimize its duration and to maximize the accuracy of characterization.

Preferably, the criteria of the method that are used by the automatic control device take account of the accuracy of the temperature measurement, that is to say of the accuracy in determining the slope of the temperature evolution. The lower the accuracy of the measurement, the longer the measurement time must be to ensure correct slope determination. During the cooling phases, the criterion must be defined in such a way that the absolute value of the slope has a maximum value, any quasi-zero slope having to be proscribed.

In an advantageous manner, in the case of a device using heating systems and sensors internal to the premises, it may be envisaged to optimize the driving of the heating by the automatic control device as a function of the occupancy of the premises and of its thermal performance K and C.

One subject of the invention is also a medium for recording information, comprising instructions for the implementation, within the framework of a method such as described hereinabove:
  of the steps of computing the heat loss coefficient K of the premises on the basis of acquired temperature measurements, and
  of the steps of automatic control of the power source as a function of the acquired temperature measurements,
when these instructions are executed by an electronic computation unit.

Figure 1:
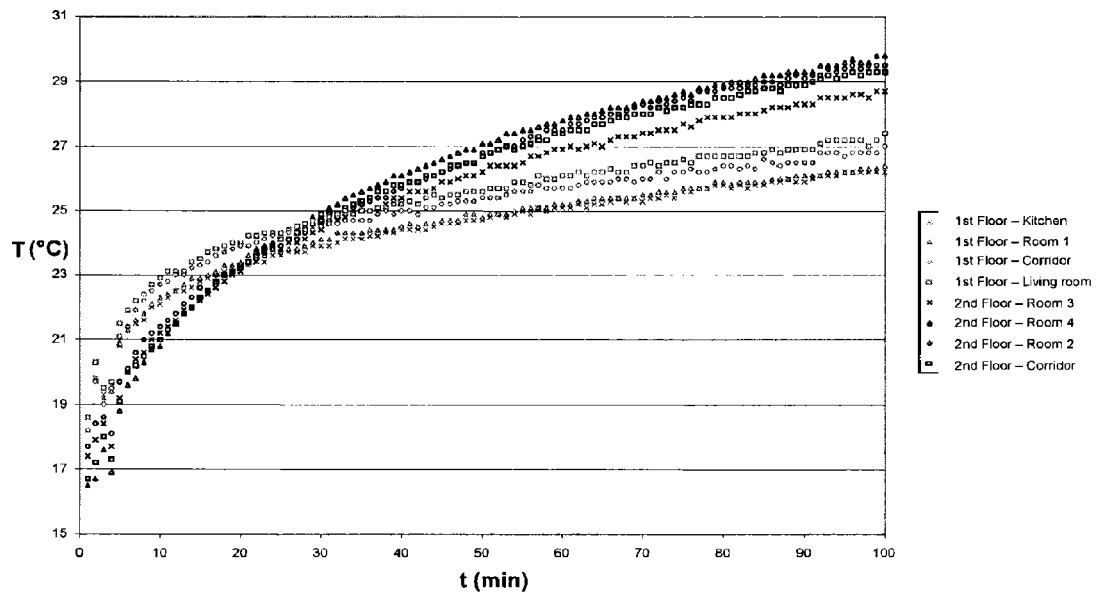
FIGS. 1 and 2 graphically illustrate the advantages, for obtaining homogeneous heating of a premises, of the use of a heating system which heats the mass of the premises directly.
Figure 2:
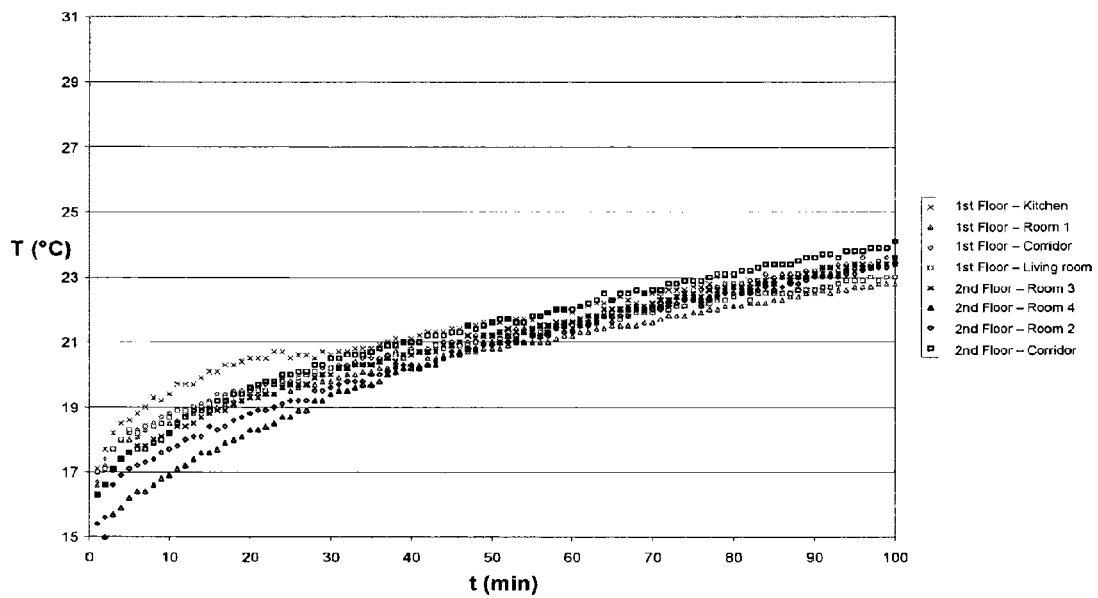
Figure 3:
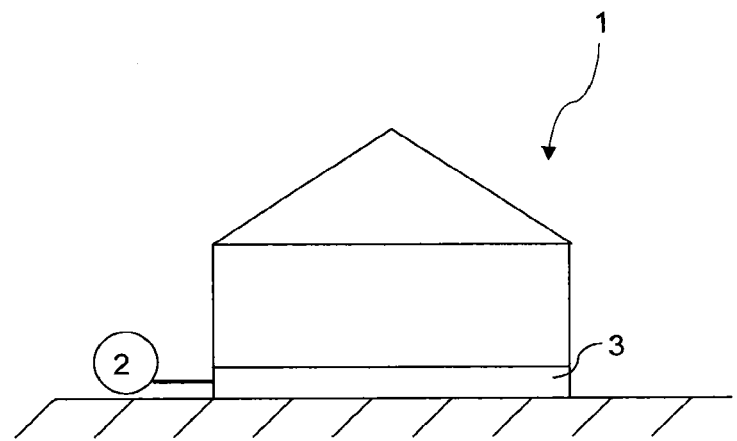
Figure 7:
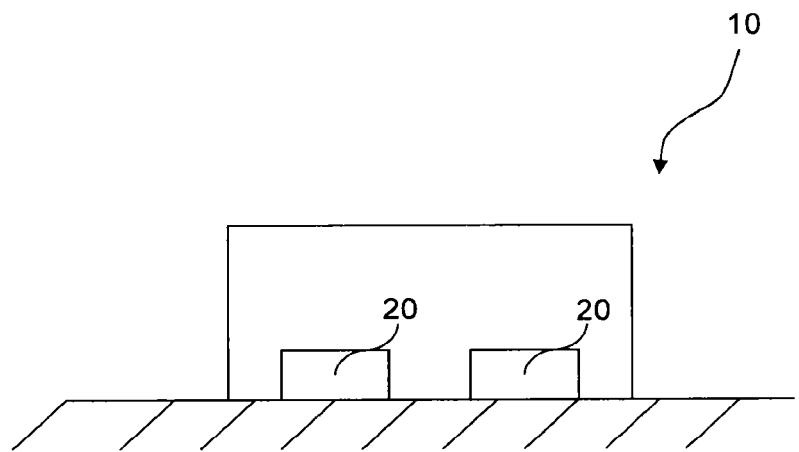
Figure 4:
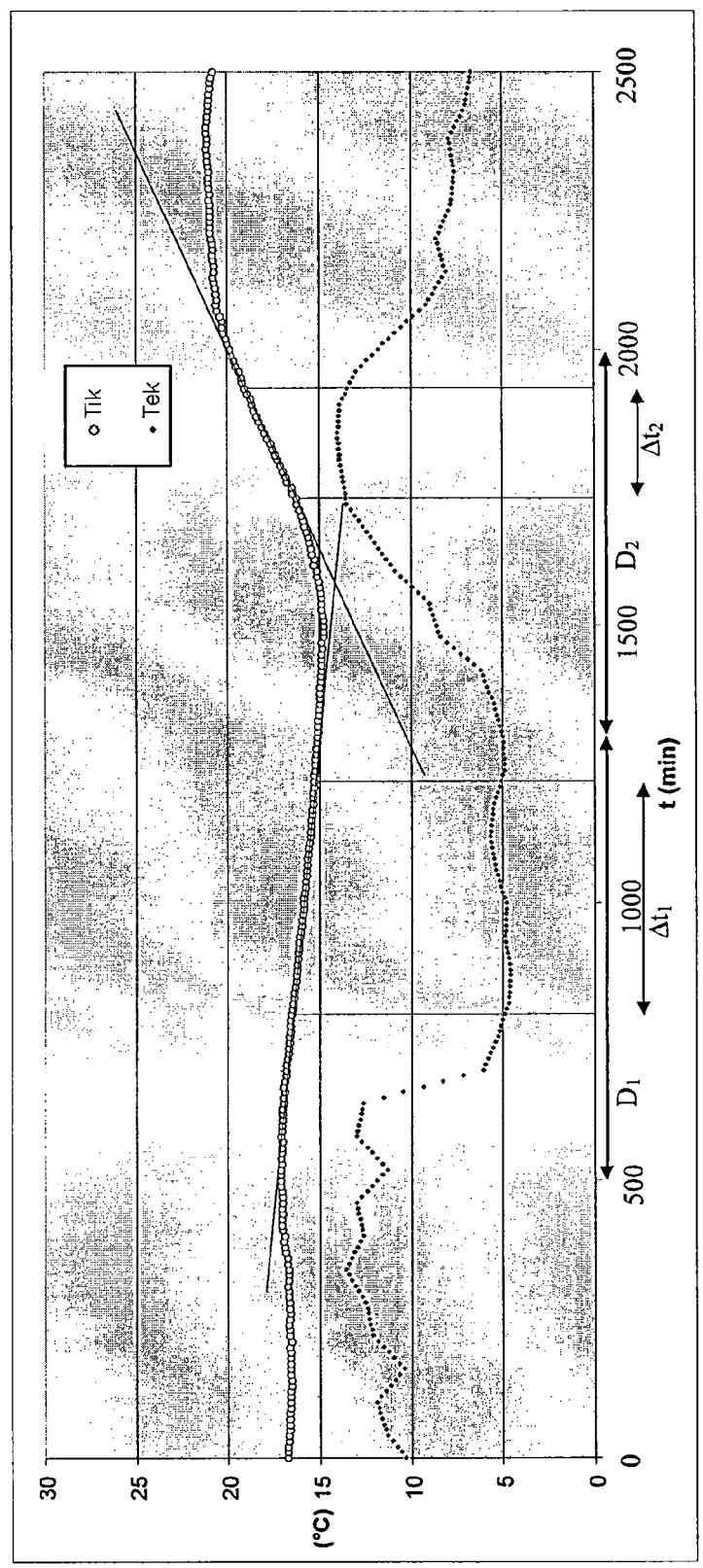
Figure 5:
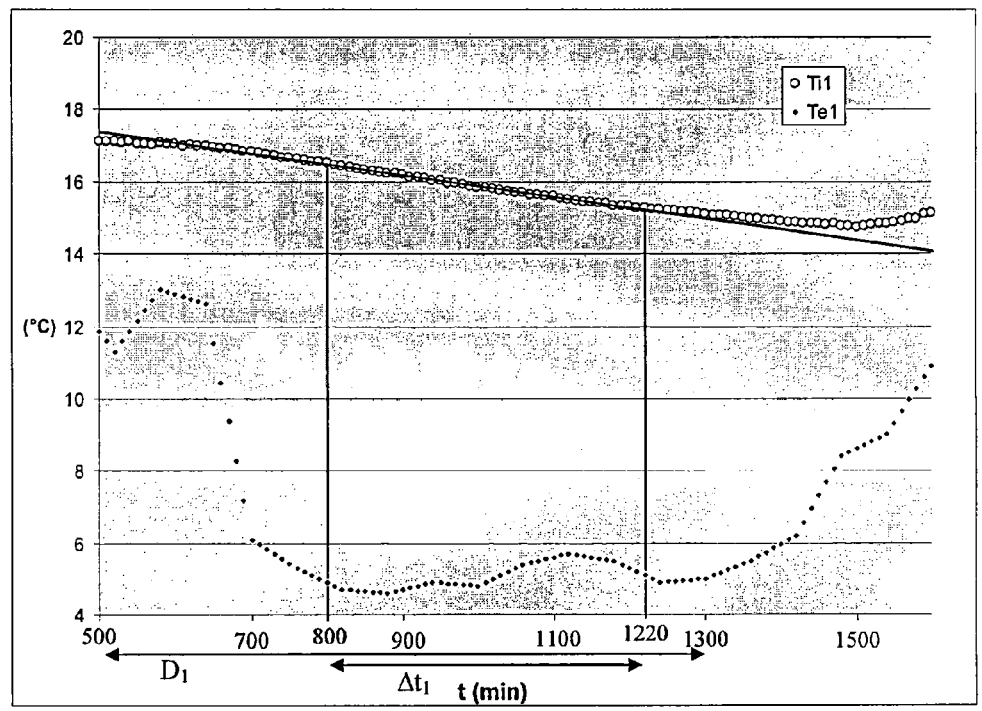
Figure 6:
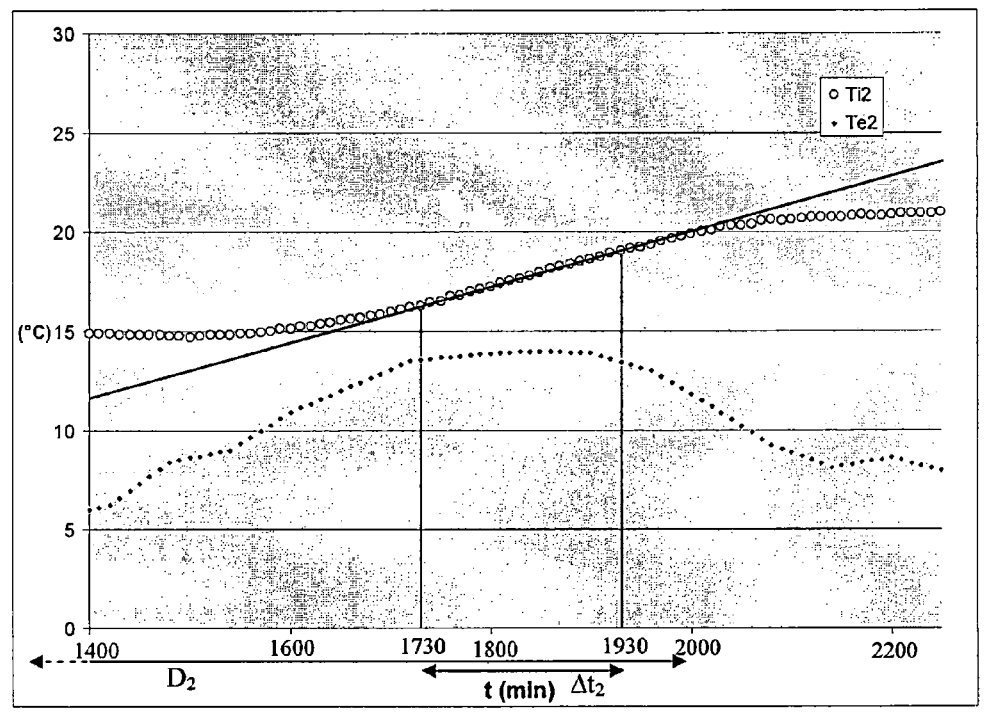
Figure 8:
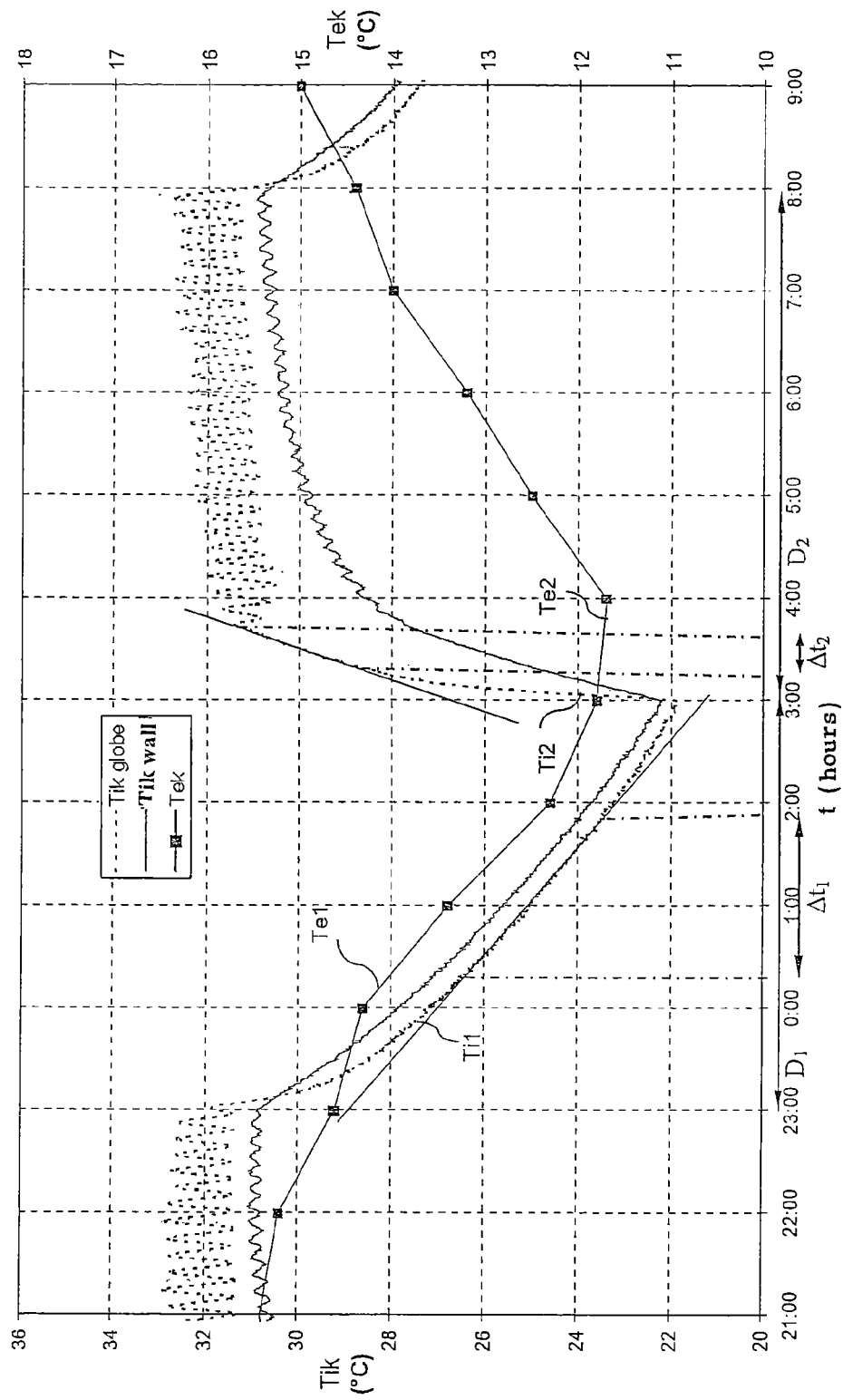

The features and advantages of the invention will be apparent in the following description of several embodiments of a method and of a device according to the invention, given solely by way of example and made with reference to the appended FIGS. 1 to 8 in which:

FIG. 3 is a schematic view of an individual house whose heat loss coefficient K it is desired to determine in accordance with the invention, this house being equipped with a heat pump as controlled power source which feeds a floor-based heating system;

FIG. 4 is a curve representative of the evolution of the temperature $T_{ik}$ inside the house of FIG. 3 as a function of time, in the course of the implementation of the method in accordance with the invention;

FIG. 5 is a curve representative of the evolution of the temperature $T_{i1}$ inside the house of FIG. 3 as a function of time, for a first time period $D_1$ in the course of which a zero imposed heating power $P_{imp1}$ is applied in the house, that is to say this first time period corresponds to an absence of heating in the house;

FIG. 6 is a curve representative of the evolution of the temperature $T_{i2}$ inside the house of FIG. 3 as a function of time, for a second time period $D_2$ in the course of which a non-zero imposed heating power $P_{imp2}$ is applied in the house;

FIG. 7 is a schematic view of a bungalow whose heat loss coefficient K it is desired to determine in accordance with the invention, the heating of the bungalow being ensured by electric convectors; and FIG. 8 is a curve representative of the evolution of the temperature $T_{ik}$ inside the bungalow of FIG. 7 as a function of time in the course of the implementation of the method in accordance with the invention, showing a first time period $D_1$ in the course of which a zero imposed heating power $P_{imp1}$ is applied in the bungalow, that is to say this first time period corresponds to an absence of heating in the bungalow, followed by a second time period $D_2$ in the course of which a non-zero imposed heating power $P_{imp2}$ is applied in the bungalow.

DETAILED DESCRIPTION

Example 1

With reference to FIG. 3, the method according to the invention is implemented for the determination of the heat loss coefficient K of an individual house 1 of recent construction, equipped with a heat pump 2. The heat pump 2 feeds a floor-based heating system 3 allowing homogeneous heating of the house. In particular, the floor-based heating system 3 ensures heating of the house 1 such that the temperature of the walls inside the house is substantially equal to the temperature of the ambient air inside the house. The heat loss coefficient K of the house 1 may be sought within the framework of a diagnosis of the energy performance of the house, for example to verify that the house 1 satisfies certain quality labels in terms of thermal insulation, such as the BBC label or the Passivhaus label.

The heating power provided by the heat pump 2 for the heating of the house is readily determinable, in particular on the basis of the COP of the heat pump as explained previously. The heat pump 2 therefore constitutes a controlled power source that is well adapted for generating the heating pulses for the house, that is to say the imposed heating powers $P_{impk}$, which are required by the method of the invention. In this example, the value of the COP of the heat pump 2 is equal to 4.23.

The method for the determination of the heat loss coefficient K of the house 1 is implemented whilst the house is unoccupied. Moreover, the house 1 is equipped with a fixed ventilation system comprising two hygro-adjustable single flow controlled mechanical ventilations (CMVs), which are not deactivated during the implementation of the method. However, as the house 1 is unoccupied and the measurement periods of the method are relatively short, it may be considered that these CMVs do not work in the course of the method.

As mentioned previously, the method according to the invention is preferably implemented continuously in its entirety over a single time period. This is the case for the example represented in FIGS. 4 to 6 since, as clearly visible in FIG. 4, the second time period $D_2$ in the course of which a non-zero imposed heating power $P_{imp2}$ is applied in the house 1 immediately follows the first time period $D_1$ in the course of which a zero imposed heating power $P_{imp1}$ is applied in the house.

In the example of FIGS. 4 to 6, the method takes place over a continuous time period which lasts about 1500 minutes, and which begins at nightfall and extends into the following daytime. Over this time period of 1500 minutes, the recorded solar radiation is low since the weather was cloudy during the implementation of the method. Furthermore, all the shutters of the house were closed during the implementation of the method. Under these conditions, the contribution of the solar radiation to the heating of the house 1 may be neglected.

Moreover, no power source other than that used for the application of the heating pulses is active in the house 1 in the course of the method. Thus, for each time period $D_1$ and $D_2$, the only power to be considered in the energy balance is the imposed heating power $P_{imp1}$ or $P_{imp2}$.

In a first step of the method, which corresponds to the first time period $D_1$, the zero first imposed heating power $P_{imp1}$ is applied in the house 1, commencing from a starting temperature $T_{i1d}=17°$ C., that is to say the heating system 3 does not operate during this period $D_1$. The ambient temperature inside the house $T_{i1}$ is then measured every ten minutes in two different rooms of the house, namely a main room and a bedroom. For this purpose, a temperature sensor is installed in each of these two rooms, in the ambient air at a height of 180 cm.

In this example, the measured evolution of the ambient temperature inside the main room and the measured evolution of the ambient temperature inside the bedroom are almost identical. Indeed, the heating of the house 1 is particularly homogeneous, so that the ambient temperature is the same in all the rooms of the house. In FIGS. 4 to 6, only the evolution of the ambient temperature inside the main room is represented, it being understood that the evolution of the ambient temperature inside the bedroom has a similar profile.

The curve representative of the evolution of the inside temperature of the house $T_{i1}$ as a function of time during the time period $D_1$ is shown in FIG. 5. As visible in this figure, the temperature fall curve for the house 1 exhibits a substantially linear part over the time interval $\Delta t_1$. Fitting an equation to this linear part of the curve gives: $T_{i1}=16.5°$ C.$-0.003$ (t$-800$), with t in minutes.

FIG. 5 also depicts the evolution of the temperature of the outside air $T_{e1}$ during the time period $D_1$. The temperature of the outside air $T_{e1}$ over the time interval $\Delta t_1$ is sufficiently stable for it to be possible to consider it substantially constant and equal to the mean temperature over the time interval $\Delta t_1$, namely in this example $T_{e1m}=5°$ C.

In a second step of the method, which corresponds to the second time period $D_2$, the heating in the house 1 is restored by applying the second imposed heating power $P_{imp2}$ in the house 1, equal to the maximum power delivered by the heat pump 2, i.e. $P_{imp2}=COP\times 5000$ W$=4.23\times 5000$ W, commencing from a starting temperature $T_{i2d}=15°$ C. As in the first step, the ambient temperature inside the house $T_{i2}$ is then measured every ten minutes, by means of two temperature sensors installed respectively in the main room and in the bedroom of the house, each time in the ambient air at a height of 180 cm. Here again, the measurements show that the evolution of the ambient temperature inside the main room and the evolution of the ambient temperature inside the bedroom are almost identical.

FIG. 6 shows the curve representative of the evolution of the inside temperature of the house $T_{i2}$ as a function of time during the time period $D_2$. As visible in this figure, the temperature rise curve for the house 1 exhibits a substantially linear part over the time interval $\Delta t_2$. Fitting an equation to this linear part of the curve gives: $T_{i2}=16.2°$ C.+0.014 (t−1730), with t in minutes.

The evolution of the temperature of the outside air $T_{e2}$ during the same time period $D_2$ is also shown in FIG. 6. As in the first step, the temperature of the outside air $T_{e2}$ over the time interval $\Delta t_2$ is sufficiently stable for it to be possible to consider it substantially constant and equal to the mean temperature over the time interval $\Delta t_2$, namely in this example $T_{e2m}=14°$ C.

The ratio $$\frac{\alpha_1}{\alpha_2}$$

of, on the one hand, the slope $\alpha_1$ of the straight line representative of the evolution of the quantity $T_{i1}(t)$ to, on the other hand, the slope $\alpha_2$ of the straight line representative of the evolution of the quantity $T_{i2}(t)$ therefore equals $$\frac{\alpha_1}{\alpha_2} = -\frac{0.003}{0.014}.$$

As the ratio of the slopes $$\frac{\alpha_1}{\alpha_2}$$

is equal to $$\frac{P_{tot1} - \theta_{1m} \cdot K}{P_{tot2} - \theta_{2m} \cdot K}$$

according to the previous equation (2), by taking $\theta_{1m}=10.9°$ C., $\theta_{2m}=3.9°$ C., $P_{imp1}=0$ W, $P_{imp2}=4.23\times5000$ W, the value of the heat loss coefficient K of the house 1 is obtained:

$K_{calc}=386$ W/K.

In practice, the steps of acquiring the inside temperature $T_{ik}$ and outside temperature $T_{ek}$ and of computing the heat loss coefficient K on the basis of the acquired temperatures may be carried out by means of a microprocessor or any other appropriate electronic computation unit.

The heating having been supplied via the mass of the building, relation (4) is applicable and, with $h_i=8$ W/m².K and $A_T=736$ m², we obtain:

$K_{corr}=362$ W/K.

The value of the heat loss coefficient $K_{corr}$ of the house 1 determined by the method of the invention may be compared with a mean static value $K_s$ of the heat loss coefficient. This mean static value $K_s$ is estimated on the basis of the energy consumption of the heat pump 2, which is measured once a week for thirteen winter weeks, in the occupied configuration of the house and for an imposed static temperature inside the house $T_{is}$ of 20° C. By deducting the share of consumption due to the sanitary hot water, the mean static value $K_s$ of the heat loss coefficient is estimated at about 430 W/K. This mean static value $K_s$ is indeed of the same order of magnitude as the value of the heat loss coefficient $K_{corr}$ determined by the method of the invention.

The difference between the two values $K_s$ and $K_{corr}$ may originate from the different occupancy conditions of the house 1 for, on the one hand, the implementation of the method in accordance with the invention and, on the other hand, the evaluation of the mean static value $K_s$. Indeed, the method of the invention has been implemented in the unoccupied house, while the mean static value $K_s$ has been evaluated with the house occupied by four people, thus implying additional energy contributions, in particular in terms of air renewal flow rate due to the hygro-adjustable CMVs, and in terms of power due to the solar radiation or to the operation of domestic electrical appliances.

A blower door test has also been carried out on the house 1. This test leads to a value of the indicator n50 of 7.35 for a heated volume of the house 1 of 688 m³. With the aid of relation (3), it is then possible to deduce the mean value of the air renewal flow rate m' in the house 1:

m'=250 m³/h.

It follows from this that the contribution of the air infiltrations represents:

m'.Cp=85 W/K.

By assuming that the two hygro-adjustable CMVs of the house 10 did not work in the course of the time periods $D_1$ and $D_2$, it may be deduced that the contribution of the heat losses by transmission is:

$H_T=UA_T=K_{corr}-m'.Cp=277$ W/K.

Furthermore, the method of the invention makes it possible to derive the value of the inertia or effective heat capacity C of the house 1 as defined previously, namely the energy necessary to increase the ambient temperature of the house by 1 K at constant outside temperature:

C=80 MJ/K.

Example 2

With reference to FIGS. 7 and 8, the method according to the invention is implemented for the determination of the heat loss coefficient K of a bungalow 10 which has an interior volume $V_i$ of 5.8 m×2.1 m×2.6 m and which is fitted with two triple-glazed windows. The envelope of the bungalow 10 consists of insulating sandwich panels assembled via a metallic structure. An additional insulation has been added to the envelope, in the form of a 40 mm thickness of glass wool and of a plasterboard as interior lining of the envelope. The permeability to air, measured by tracer gas, is 0.43 vol/h. The method is implemented whilst the bungalow is unoccupied.

The heating of the bungalow 10 is ensured by electric convectors 20 having a measured actual power of 1880 W. The convectors make it possible to heat the air in the bungalow and, on account of the limited volume of the bungalow, the heating of the bungalow is homogeneous. The convectors 20 constitute a controlled power source that is well adapted for generating the heating pulses for the bungalow, that is to say the imposed heating powers $P_{impk}$, which are required by the method of the invention. During heating, the setting is 32° C., measured by a black globe placed at the center of the air volume.

The method according to the invention is implemented continuously in its entirety over a single nocturnal time period, so as to circumvent the contribution of the solar radiation to the heating of the bungalow 10. Commencing from an inside temperature of the bungalow $T_{i1d}=32°$ C., a cooling of the bungalow is undertaken over a first time period $D_1$ from 11 pm to 3 am, this corresponding to a zero imposed heating power $P_{imp1}$, and then a heating of the bungalow is undertaken over a second time period $D_2$ from 3 am to 8 am with an imposed heating power $P_{imp2}$ of 1880 W. The second time period $D_2$ thus immediately follows the first time period $D_1$.

No power source other than that used for the application of the heating pulses is active in the bungalow 10 in the course of the method. Thus, for each time period $D_1$ and $D_2$, the only power to be considered in the energy balance is the imposed heating power $P_{imp1}$ or $P_{imp2}$.

In a first step of the method, which corresponds to the first time period $D_1$, the zero first imposed heating power $P_{imp1}$ is applied in the bungalow 10, commencing from the starting temperature $T_{i1d}=32°$ C., that is to say the convectors 2 do not operate during this period $D_1$. The ambient temperature inside the bungalow $T_{i1}$ is then measured every ten seconds. For this purpose, a black globe is placed at the center of the bungalow.

The curve representative of the evolution of the inside temperature of the bungalow $T_{i1}$ as a function of time during the time period $D_1$ is shown in FIG. 8. As visible in this figure, the temperature fall curve of the bungalow 10 exhibits a substantially linear part over the time interval $\Delta t_1$. The fitting of an equation to this linear part of the curve gives: $T_{i1}=26.5°$ C.$-0.00053$ t, with t in seconds.

FIG. 8 also depicts the evolution of the temperature of the outside air $T_{e1}$ during the time period $D_1$. The temperature of the outside air $T_{e1}$ over the time interval $\Delta t_1$ is sufficiently stable for it to be possible to consider it substantially constant and equal to the mean temperature over the time interval $\Delta t_1$, namely in this example $T_{e1m}=13.4°$ C.

In a second step of the method, which corresponds to the second time period $D_2$, the heating in the bungalow 10 is restored by applying the second imposed heating power $P_{imp2}$ in the bungalow, equal to 1880 W, commencing from a starting temperature $T_{i2d}=22°$ C. As in the first step, the ambient temperature inside the house $T_{i2}$ is then measured every ten seconds, by means of a black globe placed at the center of the bungalow.

FIG. 8 shows the curve representative of the evolution of the inside temperature of the bungalow $T_{i2}$ as a function of time during the time period $D_2$. As visible in this figure, the temperature rise curve of the bungalow 10 exhibits a substantially linear part over the time interval $\Delta t_2$. The fitting of an equation to this linear part of the curve gives: $T_{i2}=28.9°$ C.$+0.00179$ t, with t in seconds.

The evolution of the temperature of the outside air $T_{e2}$ during the same time period $D_2$ is also shown in FIG. 8. As in the first step, the temperature of the outside air $T_{e2}$ over the time interval $\Delta t_2$ is sufficiently stable for it to be possible to consider it substantially constant and equal to the mean temperature over the time interval $\Delta t_2$, namely in this example $T_{e2m}=11.8°$ C.

The ratio $$\frac{\alpha_1}{\alpha_2}$$

of, on the one hand, the slope $\alpha_1$ of the straight line representative of the evolution of the quantity $T_{i1}(t)$ to, on the other hand, the slope $\alpha_2$ of the straight line representative of the evolution of the quantity $T_{i2}(t)$ therefore equals $$\frac{\alpha_1}{\alpha_2}=-\frac{0.00053}{0.00179}.$$

As the ratio of the slopes $$\frac{\alpha_1}{\alpha_2}$$

is equal to $$\frac{P_{tot1}-\theta_{1m}\cdot K}{P_{tot2}-\theta_{2m}\cdot K}$$

according to the previous equation (2), by taking $\theta_{1m}=11.7°$ C., $\theta_{2m}=18.1°$ C., $P_{imp1}=0$ W, $P_{imp2}=1880$ W, the value of the heat loss coefficient $K_{calc}$ of the bungalow 10 is obtained:

$K_{calc}=32.6$ W/K.

In practice, the steps of acquiring the inside temperature $T_{ik}$ and outside temperature $T_{ek}$ and of computing the heat loss coefficient K on the basis of the acquired temperatures may be carried out by means of a microprocessor or any other appropriate electronic computation unit.

In this example, the interior air of the bungalow 10 is heated and, in order to compute the heat loss coefficient, use is made of black globe inside temperatures which are close to the temperatures of the ambient air inside the bungalow. Hence, it is not necessary to correct the computed value of the heat loss coefficient $K_{calc}$ with relation (4).

The value of the heat loss coefficient $K_{calc}$ of the bungalow 10 determined by the method of the invention may be compared with a mean static value $K_s$ of the heat loss coefficient. This mean static value $K_s$ is estimated under steady conditions. In practice, it is considered that steady conditions are reached when the temperature of the walls of the bungalow is stable, the temperature of the air then being likewise. The estimation of $K_s$ was done in the course of a long trial during which the mean power $P_m$ necessary to maintain the ambient temperature inside the bungalow $T_i$ stable was measured for a period of 8 hours from 11 pm to 7 am, the temperature of the outside air $T_e$ preferably also being stable during this period. The mean static value $K_s$ of the heat loss coefficient is thereafter estimated on the basis of the relation:

$P_m=K_s A_T(T_i-T_e)$.

The mean static value $K_s$ thus estimated of the heat loss coefficient is of the order of 32.7 W/K, this being close to the value of the heat loss coefficient $K_{calc}$ as determined by the method of the invention. This validates the model used.

The mean value of the air renewal flow rate m' in the bungalow is:

m'=0.43 $V_i$=13.62 m$^3$/h.

It follows from this that the contribution of the air infiltrations represents:

m'.Cp=4.6 W/K.

It may be deduced that the contribution of the heat losses by transmission is:

$H_T = UA_T = K_{calc} - m'.Cp = 28.0$ W/K.

Furthermore, the method of the invention makes it possible to derive the value of the inertia or effective heat capacity C of the bungalow 10 as defined previously, namely the energy necessary to increase the ambient temperature of the bungalow by 1 K at constant outside temperature:

$C = 720$ kJ/K.

By way of comparative example, the method according to the invention was implemented again for the bungalow 10, but this time the bungalow 10 is fitted with two plasterboards as interior lining of the envelope of the bungalow, instead of a single plasterboard as previously. All the other parameters are identical, in particular the permeability to air measured by tracer gas is still 0.43 vol/h and the method is implemented continuously in its entirety over a single nocturnal time period during which the bungalow is unoccupied. The heating-cooling cycles are the same as previously.

The value of the heat loss coefficient $K_{calc}$ of the bungalow 10 then obtained is:

$K_{calc} = 30.1$ W/K.

The contribution of the air infiltrations still being $m'.Cp = 4.6$ W/K, it may be deduced that the contribution of the heat losses by transmission is:

$H_T = UA_T = K_{calc} - m'.Cp = 25.5$ W/K.

The value of the inertia or effective heat capacity C of the bungalow fitted with two plasterboards as interior lining, namely the energy necessary to increase the ambient temperature of the bungalow by 1 K at constant outside temperature, is then:

$C = 1071$ kJ/K, this corresponding to an increase of the order of 350 kJ/K in the effective heat capacity of the bungalow with respect to the same bungalow fitted with a single plasterboard as interior lining. An estimation of the plaster area added in order to go from one to two plasterboards as interior lining of the bungalow indicates an addition of inertia of 400 kJ/K. Thus, it emerges that the method according to the invention is capable of discriminating K and C.

Example 3

In order to verify the validity of the assumptions upon which the method of the invention rests, virtual trials have been carried out with the TRNSYS software on a fictitious house having an inhabited part of 12.10 m×9.90 m×2.50 m and a total loss area $S = 350$ m². More precisely, two series of computations have been performed:
  a first series corresponding to steady conditions obtained with a non-realistic weather file, with no sun and by fixing the outside temperature at 10° C. and the power at 30 kW during the time required for the temperatures to stabilize (400 hours at the maximum);
  a second series corresponding to transient conditions obtained with a realistic weather file, namely 3 days in March for a climate matched to the town of Chambéry, by supplying power distributed homogeneously, either via the floor at the surface (not depth-wise), or via the air, of 30 kW from 7 pm to midnight, and of 3 kW during the following 36 hours, after regulation to 19° C. for a day.

The two series of trials were carried out without occupancy or internal heat supply. Each time, the infiltrations were firstly not taken into account, and then they were.

The steady case makes it possible to obtain the theoretical heat loss coefficient K of the house. By considering heating via the air and no infiltration, we obtain $K_{calc} = 167$ W/K. Under the same conditions in the transient case, by applying the method in accordance with the invention, we obtain $K_{calc} = 164$ W/K, i.e. less than 2% difference with the value obtained in the steady case. This validates that the method according to the invention furnishes a good estimation of the heat loss coefficient K.

By repeating the two series of computations under the same conditions, but with supply of heat via the floor instead of the air, we obtain respectively $K_{calc} = 177$ W/K in the steady case, and $K_{calc} = 181$ W/K in the transient case by applying the method in accordance with the invention. By considering that the coefficient of convective exchange h between the walls and the ambient air is 8 W/m².K and by using relation (4), we obtain $K_{corr} = 166$ W/K in the steady case and $K_{corr} = 170$ W/K in the transient case. This validates the fact that the direct heating of the mass of the premises may be used in the absence of infiltrations.

Finally, by considering a more realistic case, with supply of heat via the floor and infiltrations of 0.4 vol/h, we obtain $K_{calc} = 220$ W/K in the transient case by applying the method in accordance with the invention. By making the assumption that it is possible to apply the correction of relation (4) described previously even in the presence of infiltrations, to take account of the heat exchange between the walls and the ambient air with the convective exchange coefficient h taken at 8 W/m².K, we obtain $K_{corr} = 204$ W/K at the air level. By taking account of the value of the infiltrations of 0.4 vol/h = 120 m³/h, the loss by infiltrations is 120 m³/h/3600 s×1.2 kg/m³×1 kJ/kg/K = 0.04 kJ/s.K = 40 W/K. The heat loss coefficient of the envelope alone is then 204 W/K − 40 W/K = 164 W/K, a value very close to that estimated under steady conditions. This validates the fact that the direct heating of the mass of the premises may be used even in the presence of infiltrations, and that it is possible by measuring these infiltrations to separate the heat losses by transmission and the losses by infiltrations.

The invention is not limited to the examples described hereinabove. In particular, as already mentioned, the method according to the invention may be implemented equally with heating means with which the premises are equipped in a fixed manner or with heating means which are brought into the premises specifically for the implementation of the method, as long as the power provided by these heating means for the pulses required by the method can be accurately determined. Thus, in the example of the house 1, the method according to the invention could have been implemented by deactivating the heating system using the heat pump 2 of the house and by applying the heating pulses by means of a heating device brought into the house, such as a device comprising electrical heating films or else a device combining electrical heating appliances of convective type and fans.

As illustrated previously, when the value of the effective heat capacity of the premises C is not known, the method of the invention involves at least two different imposed heating powers $P_{impk}$ of the premises. Preferably, the difference between the two imposed powers $P_{impk}$ is maximized. Thus, in the previous examples, a maximum power and a zero power have been selected. As a variant, it would have been possible to choose two non-zero imposed powers $P_{impk}$, in particular a relatively low heating power and a maximum heating power.

Moreover, in the case of a premises of large size, such as an apartment building with multiple floors, the method of the invention may be used either for the determination of the heat loss coefficient K of the premises as a whole, in which case the heating and the intermingling of the air must be ensured throughout the premises, or for the determination of the heat loss coefficient K of just a part of the premises. Thus, in the case of an apartment building, it is possible to test just one apartment in the building. Accordingly, it is necessary:

either to take into account the heat losses via computation, on condition however that the parts adjoining the measured apartment are in a thermal state representative of their normal occupancy state, in particular that the normally inhabited adjoining parts are at an ambient temperature of the order of 20° C.;

or to minimize the heat losses as far as possible, for example by over-insulating the adjoining walls by means of added insulation, or else by conditioning the adjoining parts in the same manner as the measured apartment so as to ensure a temperature difference on either side of the adjoining wall that is as close to zero as possible.

Finally, as emerges from the previous examples, the method according to the invention is very suitable for the determination of the heat loss coefficient K of premises exhibiting good thermal insulation. In this case, it is indeed easy to dissipate a thermal power such that the curve $T_{ik}(t)$ may be considered to be a straight line. For other configurations of premises, in particular old and less well thermally insulated premises, the response time to the heating pulses $P_{impk}$ may be too short for the evolution of the quantity $T_{ik}(t)$ to be considered linear. The non-linear evolution of $T_{ik}(t)$ can then be modeled by an exponential of the type $$\left(\theta_k(0) - \frac{P_{impk}}{K}\right)\exp(-t/\tau)$$

over at least one time interval $\Delta t_k'$, where $$\tau = \frac{K}{C}$$

is the thermal time constant of the premises. It is possible to determine the coefficient K by applying a single heating pulse for the premises, with a necessarily non-zero power $P_{impk}$, the scheme consisting thereafter in determining the value K* of the coefficient K such that the curve $$Ln\left[\frac{\theta_k(t) - \frac{P_{impk}}{K^*}}{\theta_k(0) - \frac{P_{impk}}{K^*}}\right]$$

is a straight line, where $\theta_k(t)=T_{ik}(t)-T_{ekm}'$ and $T_{ekm}'$ is the average of the temperature measurements of the outside air $T_{ek}$ over the time interval $\Delta t_k'$.

The invention claimed is:

1. A method for determining heat loss coefficient K of a premises, comprising:
in unoccupied premises, performing a campaign of measurements of at least one temperature inside the premises $T_{ik}$ at closely-spaced time intervals over at least two successive time periods $D_k$ corresponding to distinct heating powers $P_{totk}$ of the premises, including imposing, during a first of the time periods $D_k$, a first heating power of the premises via a controlled power source and imposing, during a second of the time periods $D_k$, a second heating power of the premises via the controlled power source, the second heating power being different from the first heating power;
determining temperature of outside air $T_{ek}$ at the closely-spaced time intervals;
for each time period $D_k$, on the basis of the evolution $T_{ik}(t)$ of the quantity $T_{ik}$ as a function of time:
either, if there exists a time interval $\Delta t_k$ for which the evolution $T_{ik}(t)$ is substantially linear, determining the slope $\alpha_k$ of the tangent to the curve $T_{ik}(t)$ over this time interval $\Delta t_k$ and deducing the value of the heat loss coefficient K of the premises on the basis of the slopes $\alpha_k$;
or, if there does not exist any time interval for which the evolution $T_{ik}(t)$ is substantially linear, selecting a time interval $\Delta t_k'$ over which the evolution $T_{ik}(t)$ is substantially exponential of type $\exp(-t/\tau)$, with $\tau$ the thermal time constant of the premises, and deducing the value of the heat loss coefficient K of the premises, which is the value such that the curve $$Ln\left[\left(\theta_k(t) - \frac{P_{totk}}{K}\right) \bigg/ \left(\theta_k(0) - \frac{P_{totk}}{K}\right)\right]$$

is a straight line, with $\theta_k(t)=T_{ik}(t)-T_{ekm}'$ is the average of the temperature measurements of the outside air $T_{ek}$ over the time interval $\Delta t_k'$; and
diagnosing a thermal insulation of the premises based on the value of the heat loss coefficient K and, upon conclusion of the diagnosis, outputting a report of the diagnosis of the thermal insulation.

2. The method as claimed in claim 1, comprising:
in the unoccupied premises and over two successive time periods $D_1$ and $D_2$, performing:
over the first time period $D_1$, application of the first heating power, a campaign of measurements of at least one temperature inside the premises $T_{i1}$ at closely-spaced time intervals, and determination of the temperature of the outside air $T_{e1}$ at the same closely-spaced time intervals; and then
over the second time period $D_2$, application of the second heating power, a campaign of measurements of at least one temperature inside the premises $T_{i2}$ at closely-spaced time intervals, and determination of the temperature of the outside air $T_{e2}$ at the same closely-spaced time intervals;
for each of the first and second time periods $D_1$ and $D_2$, selecting a time interval $\Delta t_1$ or $\Delta t_2$ for which the evolution $T_{i1}(t)$ or $T_{i2}(t)$ is substantially linear and determining the slope $\alpha_1$ or $\alpha_2$ of the tangent to the curve $(T_{ik}(t))_{k=1\text{ or }2}$ over this time interval $\Delta t_1$ or $\Delta t_2$;
deducing the value of the heat loss coefficient K of the premises on the basis of the ratio of the slopes $$\frac{\alpha_1}{\alpha_2}.$$

3. The method as claimed in claim 2, wherein one power from among the first heating power and the second heating power is zero, while the other power is non-zero.

4. The method as claimed in claim 1, where the controlled power source is a fixed item of equipment of the premises.

5. The method as claimed in claim 1, wherein the controlled power source is a source brought into the premises specifically for implementation of the method.

6. The method as claimed in claim 1, wherein, over each time period $D_k$, the temperature of the outside air $T_{ek}$ is stable.

7. The method as claimed in claim 1, wherein, over each time period $D_k$, solar radiation is weak, or is zero.

8. The method as claimed in claim 7, carried out in its entirety over a single nocturnal period.

9. The method as claimed in claim 1, wherein, over each time period $D_k$, any fixed ventilation system fitted to the premises is deactivated.

10. The method as claimed in claim 1, wherein the determination of the temperature of the outside air $T_{ek}$ at the same closely-spaced time intervals is obtained through a campaign of measurements.

11. The method as claimed in claim 1, wherein each campaign of measurements of the temperature inside the premises comprises measurements of ambient temperature, measurements of temperature of walls, and/or measurements of radiant mean temperature.

12. A device for the implementation of a method as claimed in claim 1, comprising at least one temperature sensor which measures a temperature inside the premises $T_{ik}$ and a heating device for homogeneous heating of the premises comprising the controlled power source.

13. The device as claimed in claim 12, wherein the heating device heats the heat capacity of the premises directly and the temperature sensor measures the temperature in the air inside the premises.

14. The device as claimed in claim 12, further comprising:
an electronic central unit comprising means for acquiring the temperature measurements inside the premises $T_{ik}$;
means for computing the heat loss coefficient K of the premises on the basis of the acquired temperature measurements; and
means of automatic control of the power source as a function of the acquired temperature measurements.

15. A method for determining heat loss coefficient K of a premises whose effective heat capacity C is known, where C is the energy required to increase ambient temperature inside the premises by 1K while temperature of outside air is constant, the method comprising:
in unoccupied premises, performing a campaign of measurements of at least one temperature inside the premises $T_i$ at closely-spaced time intervals over a single time period corresponding to a non-zero heating power $P_{tot}$ of the premises, including imposing the non-zero heating-power $P_{tot}$ of the premises via a controlled power source;
determining the temperature of the outside air $T_e$ at the closely-spaced time intervals;
on the basis of the evolution $T_i(t)$ of the quantity $T_i$ as a function of time:
either, if there exists a time interval $\Delta t$ for which the evolution $T_i(t)$ is substantially linear, determining the slope $\alpha$ of the tangent to the curve $T_i(t)$ over this time interval $\Delta t$ and deducing the value of the heat loss coefficient K of the premises on the basis of the slope $\alpha$ and of the effective heat capacity C of the premises;
or, if there does not exist any time interval for which the evolution $T_i(t)$ is substantially linear, selecting a time interval $\Delta t'$ over which the evolution $T_i(t)$ is substantially exponential of type $\exp(-Kt/C)$ and deducing the value of the heat loss coefficient K of the premises, which is the value such that the curve $$\mathrm{Ln}\left[\left(\theta(t) - \frac{P_{tot}}{K}\right) \Big/ \left(\theta(0) - \frac{P_{tot}}{K}\right)\right]$$

is a straight line, with $\theta(t)=T_i(t)-T_{em}'$ where $T_{em}'$ is the average of the temperature measurements of the outside air $T_e$ over the time interval $\Delta t'$; and
diagnosing a thermal insulation of the premises based on the value of the heat loss coefficient K and, upon conclusion of the diagnosis, outputting a report of the diagnosis of the thermal insulation.

* * * * *